United States Patent
Clarke et al.

[11] 4,038,086
[45] July 26, 1977

[54] AQUEOUS AMMONIACAL ZINC ARSENIC OR ZINC/COPPER ARSENIC WOOD PRESERVATIVE SOLUTIONS

[75] Inventors: Michael R. Clarke; Jaromir R. Rak, both of Ottawa, Canada

[73] Assignee: Canadian Patents and Development Limited, Ottawa, Canada

[21] Appl. No.: 568,789

[22] Filed: Apr. 16, 1975

Related U.S. Application Data

[63] Continuation-in-part of Ser. No. 362,104, May 21, 1973, Pat. No. 3,945,835.

[30] Foreign Application Priority Data

Dec. 12, 1972 Canada .................................. 158685

[51] Int. Cl.² .............................................. C09D 5/14
[52] U.S. Cl. ................................. 106/15 R; 424/133; 424/140; 424/145; 424/166; 427/440
[58] Field of Search .................... 106/15 AF; 424/134, 424/141, 133, 140, 145, 166; 427/440

[56] References Cited
U.S. PATENT DOCUMENTS

| 1,632,508 | 6/1927 | Schantz ................................. 427/291 |
| 2,194,827 | 3/1940 | Gordon ................................ 424/128 |
| 2,310,257 | 2/1943 | Ritter ................................ 106/15 AF |
| 2,414,661 | 1/1947 | Nikitin ................................ 424/177 |

FOREIGN PATENT DOCUMENTS 568,393  1/1959  Canada

Primary Examiner—Lorenzo B. Hayes
Attorney, Agent, or Firm—Flynn & Frishauf

[57] ABSTRACT

Aqueous ammoniacal wood treating compositions are provided which have a pH of 9 or more. The cations are zinc ammonium or copper ammonium and zinc ammonium ions. The anions include arsenic or arsenious ions, as well as further anions of carbonate and/or bicarbonate. The weight ratio of zinc or zinc and copper (as oxide) to arsenic (as oxide) is greater than 1.5. Preferably, the weight ratio of $CO_2/NH_3/Zn/As$ or $CO_2/NH_3/Zn+Cu/As$ is 1.7–2.3/5.9–6.7/1.9–2.9/.9. The compositions provide a treated wood product with increased leaching resistance of arsenic. Treating procedures and treated wood products are also provided.

13 Claims, 1 Drawing Figure

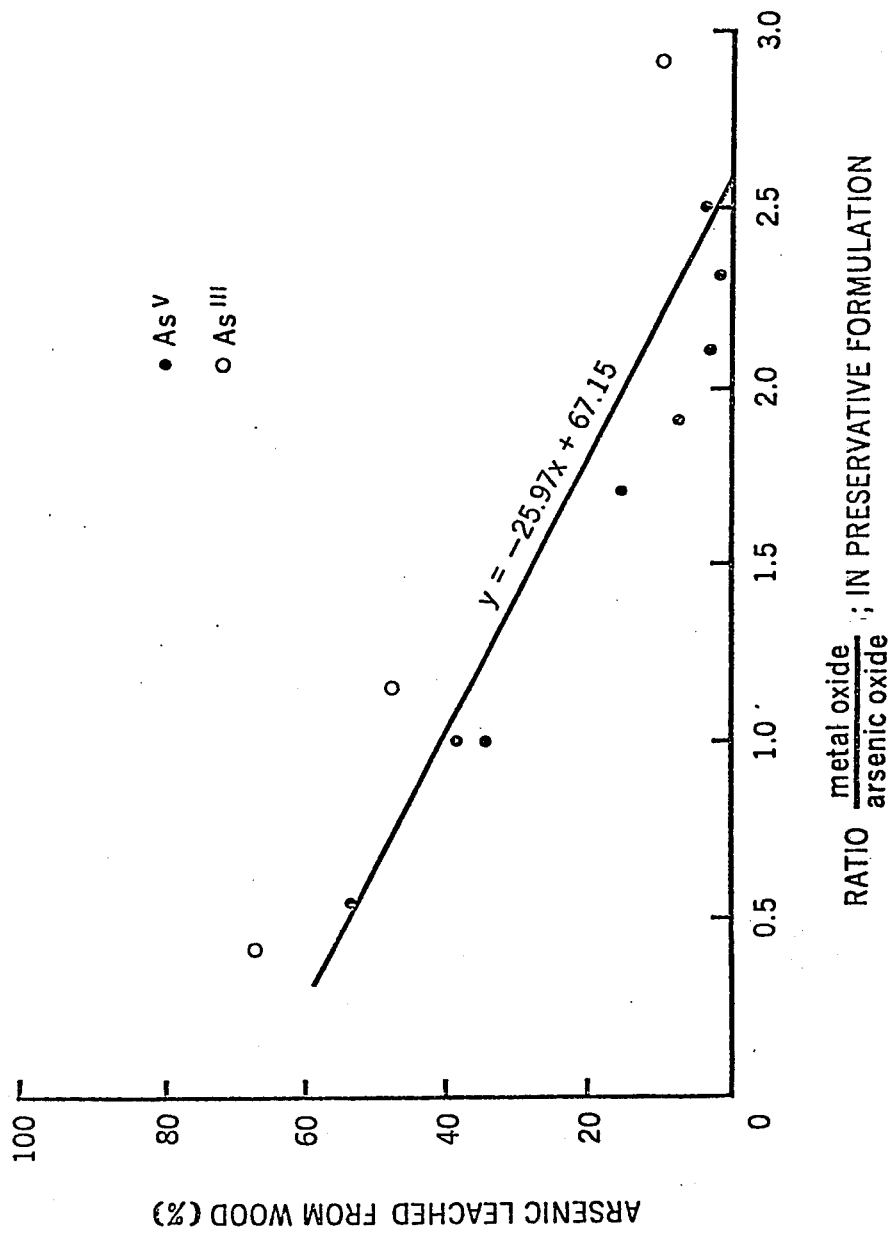

AQUEOUS AMMONIACAL ZINC ARSENIC OR ZINC/COPPER ARSENIC WOOD PRESERVATIVE SOLUTIONS

RELATED INVENTIONS

This application is a continuation-in-part of copending application Ser. No. 362,104 filed May 21, 1973 now U.S. Pat. No. 3,945,935.

BACKGROUND OF THE INVENTION i. Field of the Invention

This invention relates to compositions and procedures for the treatment of wood and wood products. Such compositions and treatment procedures are designed to provide protection not only during the storage and the handling of the lumber, or as use as a primer of sheathing, but also to provide protection during the final use of the wood and wood products. It also relates to the treated wood products so formed.

A piece of timber, due to the manner of its formation, possesses anisotropic structure which influences its properties and behaviour. Compared to competitive cladding materials, for example, metals and plastics materials, it has a number of major disadvantages which tend to counteract the advantages of strength, lightness, low thermal expansion and, in some instances, desirable aesthetic features. To overcome and minimize these disadvantages a number of specific problems exist: the wood must be protected against degrading environmental factors (namely, moisture cycling, photodegradation and biological attack); the dimensional stability with respect to moisture cycling must be improved; photodegradation due to sunlight must be minimized; the resistance to biological attack (fungus) must be improved; the adhesion of protective and decorative coatings must be improved; and extractives which adversely affect protective and decorative properties of coatings must be sealed within the wood. For some purposes, such aims should be achieved with a treatment that does not alter the natural beauty of wood.

ii. Description of the Prior Art

Protective system should impart not only protection against biological degradation, but also considerable weather resistance. The special needs for some purposes are high protection against weather, and against biodegradation and, additionally, providing protection against fire and maintaining the natural appearance of wood without discoloration after treatment. The system should provide weather resistance with enhanced glowing combustion resistance and no discoloration after treatment. The treated material should also be clean and paintable.

Four classes of treatments are currently used in an attempt to meet these requirements.

The first class is that of clear or pigmented penetrating systems which contain fungicides and water-repellent additives, such as, for example, polyethylene waxes and metal stearates in a non-aqueous solvent media. These treatments are deficient in that they must be repeated at regular intervals of 1 to 2 years to provide a desired level of protection.

The second class is that of stains and sealers. These are normally synthetic resin solutions, usually pigmented and designed to penetrate the surface of the wood. These treatments as well are deficient, and should be repeated every 1 to 2 years in order to provide the required degree of protection.

The third class is that of paint system. Such paint systems would normally consist of a primer and top coats. When well applied, these will provide the exterior cladding protection from 2 to 5 years.

The fourth class is that of salt treatments. A number of salt treatments have been suggested, the most common of which are known as copper-chrome arsenate (CCA), zinc metaarsenate (ZMA), acid-copper-chromate (ACC), and ammoniacal copper arsenite (ACA). Present systems of this type are effective to provide relatively long term durability when applied by pressure impregnation techniques. While such systems are effective in preventing biological deterioration of wood and provide clean and paintable surfaces, they, however, suffer from several disadvantages. CCA preservatives have low stability under storage and processing conditions and penetration into wood is limited. ACC preservatives cannot penetrate refractory species but water repellency of wood treated by ACC is good. Ammoniacal copper salts provide extremely stable treating solutions and produce a treated wood product which is deeply penetrated (particularly in the case of refractory species), but which provides negligible protection to the products against weathering. All systems provide products which are more or less colored; thus the natural appearance of wood is changed or covered by the colored preservative. Furthermore, none of these systems provides protection against glowing combustion. The CCA systems are believed to become fixed in the wood by oxidation-reduction reaction associated with the chromic acid in the compositions and it is these same reactions which are believed adversely to affect stability and processing characteristics. Furthermore, the arsenic-containing formulations mostly have little leach resistance, resulting in environmental pollution by leached arsenic.

A paper in the Forest Products Journal, Vol. 22, No. 11, November 1970 by M.P. Levi et al. entitled "Distribution and Effectiveness in Pinus Sp. of a Water Repellent Additive for Water-Borne Wood Preservatives" discusses the development of a water repellent additive for use with water-borne CCA preservatives to overcome the deficiency of prevention of weathering degradation.

Ammoniacal copper arsenite compositions are presently being used as preservatives. Zinc arsenate, zinc arsenite, and zinc phosphate can all be applied from an acetic acid solution and, on drying, the salt is water insoluble but very poorly fixed in the wood. However, in all of these cases, the weather resistance of the treated wood is not significantly improved.

Thus, each of the preserving systems mentioned above has disadvantages and these can be summarized as follows.

The major disadvantage of the use of copper-chrome-arsenate systems is limited stability of the treating solution under processing conditions, low penetration into difficult-to-penetrate species, and relatively low leach resistance of the arsenic.

The major disadvantage of the use of ammoniacal copper compounds is the lack of weathering resistance of the treated wood product, and very poor fixation and very low leach resistance of arsenic in treated wood.

Copper and zinc-containing fungicides which have been proposed, (see U.S. Pat. No. 2,414,661 issued Jan. 21, 1947 to A. A. Nikitin), were prepared by precipitation of a zinc salt and a copper salt from an aqueous solution with an alkali solution containing soya bean protein, or soaps of fatty acids.

Fungicides, which have been proposed for cellulosic materials, (see U.S. Pat. No. 2,423,619 issued July 8, 1947 to L. Roon), comprise copper soaps formed in situ from an aqueous solution of copper salts and aqueous ammonia by reaction with fatty acids.

It has also been proposed to provide water and fire-resistant coatings on wood, (see U.S. Pat. No. 2,530,458 issued Nov. 21, 1950 to H. R. Frisch) by the use of zinc orthophosphate or zinc orthoarsenate compositions applied as a concentrated solution in aqueous ammonia.

It has been proposed, (see U.S. Pat. No. 2,768,910 issued Oct. 30, 1956 to H. Krzikalla and O. Lissner) to improve the hardness, compressive strength, hygroscopicity and liability to swell of wood by impregnating the wood with an aqueous ammoniacal solution of polycarboxylic acid containing at least six carbon atoms.

It has been proposed, (see U.S. Pat. No. 2,772,263 issued Nov. 27, 1956 to C. C. Yeager) to use a compound having a high fungicidal activity in wood, which compound is a metal rosin ammonium phenoxide-complex metal carboxylic acid soap compound, prepared by reacting a rosin ammonium phenoxide with a water-soluble salt of a metal capable of forming a complex with ammonia.

It has also been proposed, (see U.S. Pat. No. 3,007,844 issued Nov. 7, 1961 to W. O. Schuly) to use a composition comprising a heavy metal ion, borate ions and chromate ions as an impregnating agent for the preservation of wood.

It has further been proposed, (see U.S. Pat. No. 3,105,773 issued Oct. 1, 1963 to S. Frank and D. C. Wehner) to preserve wood by imparting pesticidal and anti-thallophytic properties thereto by first impregnating the wood with a water-soluble heavy metal salt, and then with an acrylic polymer solution.

It has still further been proposed, (see U.S. Pat. No. 1,942,977 issued Jan. 9, 1934 to E. E. M. Payne) to treat wood products with a solution of one or more ammonium phosphates and then with a solution containing acid phosphates of magnesium and zinc, in order to precipitate an insoluble phosphate within the cell structure of the material, thereby to improve the color of the materials and to render the treated material resistant to fire.

It has also been proposed, [see British Pat. No. 1,220,281 published Jan. 27, 1971 in the name of Hickson's Timber Impregnation Co. (G.B.) Ltd.] to treat wood with an aqueous emulsion containing an aqueous solution of a wood preservative composition based on hexavalent chromium, a water-insoluble insecticide in a liquid hydrocarbon solvent, and a non-ionic surface active agent. The emulsion is used by impregnation of the wood by means of a pressure process, to provide protection against fungal attack and against a variety of insects.

Finally, it has been proposed, (see Canadian Pat. No. 568,393 issued Jan. 6, 1959 to B. O. Hager) to provide a wood preservative composition consisting of an ammoniacal aqueous solution containing an amine-forming metal, e.g. Cu or Cu and Zn, with or without arsenic and carbon dioxide of a content at least two-thirds of the metal content. The ratio of $CO_2/NH_3/Cu$ and/or $Zn/As$ is $1.8-5.5/3.2-4.8/1.6-2.4/0.9-0.96$.

While the use of the compositions outlined above has tended to provide a considerable level of protection against specific degrading agencies, none of them provides a suitable balance of properties such as, for example, excellent stability under processing conditions, high weather resistance, paintability, good wood penetration and good water repellency, and low arsenic leachability. Additionally, some of the compositions outlined provide in one system some measure of protection against fire and do not adversely affect the natural appearance of the treated wood.

SUMMARY OF THE INVENTION i. Aims of the Invention

Therefore, prime objectives of this invention are to provide such compositions in which a suitable balanced improvement is provided in the following properties of treated wood, namely: a good level of weather resistance; low arsenic leachability and therefore low mammalian toxicity; resistance to biological and fungal attack; resistance to water penetration; resistance to extractive staining; effective resistance to glowing combustion; good adhesion properties between the wood and a coating, e.g. paint or glue, etc. later to be applied thereto; and no substantial adverse effect on lumber seasoning.

ii. Statement of the Invention

According to a broad concept of this invention, a wood treating composition is provided which is based on zinc or zinc and copper ammonium complexes containing arsenic anions ($As^{III}$ or $As^V$), with the weight ratio of zinc or zinc and copper (as oxides) to arsenic (as oxides) being 1.5 or more, containing carbonate or bicarbonate ions, and preferably the weight ratio of $CO_2/NH_3/Zn/As$ or $CO_2/NH_3/Zn+Cu/As$ being $1.7-2.3/5.9-6.7/1.9-2.9/.9$, all components being soluble in one common aqueous ammoniacal solution. In the above-noted composition, the preservative compounds in the form of water-insoluble salts of zinc or a mixture of zinc and copper are solubilized in admixture with certain specified water repellent compounds in the ammoniacal solution.

iii. Other Features of the Invention

In other words, in a broad aspect of this invention, a wood treating composition is provided, comprising an aqueous solution containing (a) a normally water-insoluble compound of zinc or zinc and copper with arsenic acid or arsenious acid in an amount of 0.1–4% by weight (as Zn or Zn + Cu metal) of the total aqueous solution, the weight ratio of zinc or zinc and copper (as oxides) to arsenic (as oxides) being 1.5 or more; (b) 0.15–10% by weight of the total aqueous solution of carbonate and/or bicarbonate ions in an amount of up to 150% of the zinc or zinc and copper; and (c) ammonia, in an amount of 1–28% by weight of the total aqueous solution; and the weight ratio of $CO_2/NH_3/Zn/As$ or $CO_2/NH_3/Zn + Cu/As$ being $1.7-2.3/5.9-6.7/1.9-2.9/0.9$, the ammonia being sufficient to solubilize the normally water-insoluble salt of zinc or zinc and copper, and the carbonate and/or bicarbonate.

The constituents of the preservative composition may range in concentration (expressed as percentage by weight of the total) as follows:

1. Zinc or zinc and copper arsenic compound, present as the arsenate or the arsenite with the weight ratio of zinc or zinc and copper (as oxides) to arsenic (as oxides) being 1.5 or more . . . 0.1–4 (as Zn or Zn+Cu metal)

2. Carbonate and/or bicarbonate ions present in proportions ranging up to 150% of the zinc or zinc and copper . . . 0.15–10
and
3. Ammonia . . . 1–28

By another aspect of this invention, a procedure is provided for protecting wood, particularly spruce, which comprises impregnating such wood by applying an aqueous solution (as described above) to the surfaces (or interior by a hole) of such wood and then drying the wood with the resulting loss of ammonia and high fixation of arsenic.

By yet another aspect of this invention, a concentrated preservative composition is provided which includes a zinc arsenic compound or mixtures of zinc and copper arsenic compounds in which the arsenic compound is present as the arsenate or the arsenite, in which the weight ratio of zinc or zinc and copper (as oxides) to arsenic (as oxides) is 1.5 or more, a carbonate and/or bicarbonate, and concentrated aqueous ammonia, in which the amounts of the zinc and copper are directly proportional to the amount of the arsenic compound. The total metal (Zn or Cu + Zn) in the concentrate can range from about 4 up to about 15% by weight based on the volume of the solution. The concentrate is dilutable to give a treating composition as described above having a total metal content of about 0.1–4% on a weight/weight basis.

Thus, the total amount of metal in the treating solution is generally 0.1–4% on a weight/weight basis, and the total metal in the concentrate usually is from up to 4 to 15% on a weight/volume basis. The total solids in the concentration will usually be from about 15–45% by weight, based on the volume of the solution, and, on dilution, the total solids will decrease to about 1–15% on a weight/volume basis in the treating solution.

Whether zinc or zinc and copper is used, a carbonate ion and/or a bicarbonate ion is also incorporated in the composition. The carbonate ion or bicarbonate ion can be provided either by selection of the zinc carbonate, zinc bicarbonate, copper carbonate or copper bicarbonate, or it can be formed by reaction of a suitable zinc or copper salt, e.g. the oxide with ammonium carbonate or ammonium bicarbonate in the ammonia solution. In addition, the carbonate or the bicarbonate may be used as the sole additional agent. The metal is thus in an excess over the stoichiometric amount forming the arsenate or the arsenite.

If the composition within the ambit of this invention is one containing zinc ions, the wood material provided, according to another aspect of this invention, is one having high aesthetic considerations. The essential presence of arsenic acids or arsenious acids or mixtures thereof in such composition results in a composition which protects the wood against biological degradation. When carbonic and/or bicarbonate acid ions are present in the composition, the composition imparts high water repellency and weather resistance to the wood. When zinc ions with carbonic or bicarbonic acid ions or mixtures thereof are present in the composition, the composition imparts protection to the wood against glowing combustion.

If the solution is one containing copper ions, the wood material provided, according to yet another aspect of this invention, is one having low aesthetic considerations. The essential presence of arsenic acids or arsenious acids or mixtures thereof in such composition results in a composition which protects the wood against biological degradation. When carbonic and/or bicarbonic acid ions are present in the composition, the composition imparts high water repellency and weather resistance to the wood.

The level of ammonia used in the composition described above is generally in excess of that required to form the copper or zinc salts or coordinating complexes; the pH of the aqueous compositions will generally be pH 9 or higher. The non-volatile solids of the treating compositions may vary between about 1 and about 25%.

In one embodiment, compositions are provided which comprise an aqueous solution of a zinc ammonium arsenate or arsenious complex with the water repellent additive in the form of carbonate which is characterized by its ability to give rapid penetration into wood substance and which on drying leaves wood with its natural appearance and color, resistant to biological deterioration, resistant to weathering and resistant to glowing combustion. The treating solution has excellent stability under processing conditions and has been found to have very low arsenic leachability.

One example of such treating composition is:

| | | |
|---|---|---|
| arsenic oxide (III) | 1.22 | parts by weight |
| zinc oxide | 3.57 | parts by weight |
| NH₄HCO₃ | 4.12 | parts by weight |
| aqueous ammonia (28% NH₃, 20 ml in 100 ml water) | 91 | parts by weight |

Another example of such treating composition is:

| | | |
|---|---|---|
| arsenic oxide (V) | 1.42 | parts by weight |
| zinc oxide | 3.57 | parts by weight |
| NH₄HCO₃ | 4.12 | parts by weight |
| aqueous ammonia (28% NH₃, 20 ml in 100 ml water) | 91.0 | parts by weight |

For comparison purposes with copper, a composition comprises an aqueous solution of a copper ammonium arsenic or arsenious complex with the water repellent additive in the form of carbonate and/or bicarbonate, which is characterized in that it gives rapid penetration into the wood substance and which, on drying, renders the wood resistant to weathering and resistant to biological deterioration. This treating solution has excellent stability under processing conditions but has been found to have medium arsenic leachability.

One example of such composition is:

| | | |
|---|---|---|
| arsenic oxide | 1.42 | parts by weight |
| copper oxide | 2.43 | parts by weight |
| NH₄HCO₃ | 1.80 | parts by weight |
| aqueous ammonia (28% NH₃, 25 ml in 100 ml water) | 94 | parts by weight |

The compositions may be applied to the wood by known application methods, for example, by brush, spray or dip treatments or by impregnation techniques.

In use, the preservative composition impregnates the wood, and after being dried with the resulting loss of ammonia, the preservative compounds become fixed in the wood substance. The treated wood is resistant to decay and insect attack, has high water repellency, and increased protection against glowing combustion. The composition penetrates efficiently into even refractory species and on drying renders wood highly resistant to weather and to biological attack.

While it is not desired to be limited to any particular theory, it is believed that the high moisture pick-up of wood is due to physical absorption of moisture onto cellulose chains in the microfibrils, resulting in a decrease in the association between neighbouring cellulose chains. It is believed further that the composition changes the hydrophylic nature of the wood surface (both external and internal) to a hydrophobic nature and thereby increases the weather resistance of the treated wood substance.

It is felt that the reduction in moisture pick-up of the treated wood is due to a cross-linking action by the zinc or copper ions between neighbouring cellulose chains. This cross-linking action may well occur due to the high strength of coordination linkages. It is further believed that resistance to photodegradation is associated with the formation of pigment crystals formed within the wood substance which effectively screens the natural polymers from the damaging radiation.

BRIEF DESCRIPTION OF THE DRAWINGS

In the accompanying drawing, the single FIGURE is a graph of arsenic leached from wood (in %), as ordinate, and the ratio of metal oxide/arsenic oxide in the preservative formulation, as abscissa.

DESCRIPTION OF PREFERRED EMBODIMENTS AND EXAMPLES

EXAMPLES I-XI

Treating Solutions

Eleven preservative formulations were prepared as follows, and tested for the following properties of the treating solution, namely: the ability to penetrate refractory species, and stability in processing: and the following properties of the treated wood, namely: toxicity to wood decaying fungi, water repellency, leaching resistance, glowing combustion resistance and natural appearance color.

The compositions of the treating solutions tested are given in the following Examples I–XI.

Example I

| ZMA | zinc meta arsenite, commercial preservative | |
|---|---|---|
| | | ZMA ($As^{III}$) |
| Arsenic (III) oxide (g) | | 1.22 |
| ZnO (g) | | 0.50 |
| $NH_4HCO_3$ (g) | | 0.58 |
| $NH_4OH$ (28% $NH_3$; ml) | | 20 |
| $H_2O$ to volume (ml) | | 100 |
| oxide concentration (%; w/v) | | 1.72 |
| specific gravity ($g/cm^3$) | | 0.996 |
| ratio metal oxide arsenic oxide in formation | | 0.41 |

Example II

| ACA | ammoniacal copper arsenite, commercial preservative (according to the AWPA Standards) | |
|---|---|---|
| | | ACA ($As^{III}$) |
| Arsenic (III) oxide (g) | | 1.22 |
| CuO* (g) | | 1.41 |
| $NH_4OH$ (28% $NH_3$; ml) | | 25 |
| $H_2O$ to volume (ml) | | 100 |
| oxide concentration (%; w/v) | | 2.63 |
| specific gravity ($g/cm^3$) | | 0.999 |
| ratio metal oxide arsenic oxide | | |

Example II-continued

| | |
|---|---|
| in formulation | 1.16 |

Example III

| CuAs | copper-arsenic component mixture derived from Cu-As content in CCA-C formulation (AWPA Standard) | |
|---|---|---|
| | | CuAs ($As^V$) |
| Arsenic (V) oxide (g) | | 1.15 |
| CuO* (g) | | 0.62 |
| $NH_4OH$ (28% $NH_3$; ml) | | 25 |
| $H_2O$ to volume (ml) | | 100 |
| oxide concentration (%/ w/v) | | 1.77 |
| specific gravity ($g/cm^3$) | | 0.994 |
| ratio metal oxide arsenic oxide in formulation | | 0.54 |

Example IV

| $St_{CCA-C}$ | basic copper arsenate with As content derived from CCA-C formulation | |
|---|---|---|
| | | $St_{CCA-C}$ ($As^V$) |
| Arsenic (V) oxide (g) | | 1.15 |
| CuO* (g) | | 1.15 |
| $NH_4OH$ (28% $NH_3$; ml) | | 25 |
| $H_2O$ to volume (ml) | | 100 |
| oxide concentration (%; w/v) | | 2.30 |
| specific gravity ($g/cm^3$) | | 0.997 |
| ratio metal oxide arsenic oxide in formulation | | 1.00 |

Example V

| $St_{CAA}$ | basic copper arsenate with As content derived from CAA formulation | |
|---|---|---|
| | | $St_{CAA}$ ($As^V$) |
| Arsenic (V) oxide (g) | | 1.42 |
| CuO* (g) | | 1.42 |
| $NH_4OH$ (28% $NH_3$; ml) | | 25 |
| $H_2O$ to volume (ml) | | 100 |
| oxide concentration (%; w/v) | | 2.84 |
| specific gravity ($g/cm^3$) | | 0.998 |
| ratio metal oxide arsenic oxide in formulation | | 1.00 |

Example VI

| CAA | copper-ammonia-additive system containing $As^V$, basically copper arsenate with an excess of copper oxide, but, generally speaking, a new formulation | |
|---|---|---|
| | | CAA ($As^V$) |
| Arsenic (V) oxide (g) | | 1.42 |
| CuO* (g) | | 2.43 |
| $NH_4HCO_3$ (g) | | 1.80 |
| $NH_4OH$ (28% $NH_3$; ml) | | 25 |
| $H_2O$ to volume (ml) | | 100 |
| oxide concentration (%; w/v) | | 3.85 |
| specific gravity ($g/cm^3$) | | 1.030 |
| ratio metal oxide arsenic oxide in formulation | | 1.71 |

Examples VII & VIII

| ZAA ($As^{III, V}$) | zinc-ammonia-additive system containing $As^{III}$ or $As^V$, basically zinc arsenate with an excess of zinc oxide, but, generally speaking, a new formulation |
|---|---|

Examples VII & VIII-continued

| (As$^{III}$) | ZAA (As$^V$) | ZAA |
|---|---|---|
| Arsenic oxide (g) | 1.22 | 1.42 |
| ZnO (g) | 3.57 | 3.57 |
| NH$_4$HCO$_3$ (g) | 4.12 | 4.12 |
| NH$_4$OH (28% NH$_3$; ml) | 20 | 20 |
| H$_2$O to volume (ml) | 100 | 100 |
| oxide concentration (%; w/v) | 4.79 | 4.99 |
| specific gravity (g/cm$^3$) | 1.040 | 1.049 |
| ratio metal oxide arsenic oxide in formulation | 2.92 | 2.51 |

Examples IX - XI

CZAA (3:1, 1:1, 1:3)  mixture of CAA and ZAA in given volume ratios, new formulations

| | CZAA (3:1) (As$^V$) | CZAA (1:1) (As$^V$) | CZAA (1:3) (As$^V$) |
|---|---|---|---|
| Arsenic (V) oxide (g) | 1.42 | 1.42 | 1.42 |
| CuO* (g) | 1.82 | 1.21 | 0.61 |
| ZnO (g) | 0.89 | 1.79 | 2.68 |
| NH$_4$HCO$_3$ (g) | 2.38 | 2.96 | 3.54 |
| NH$_4$OH (28% NH$_3$; ml) | 23.7 | 22.5 | 21.2 |
| H$_2$O to volume (ml) | 100 | 100 | 100 |
| oxide concentration (%; w/v) | 4.13 | 4.42 | 4.71 |
| specific gravity (g/cm$^3$) | 1.034 | 1.039 | 1.043 |
| ratio metal oxide arsenic oxide in formulation | 1.91 | 2.11 | 2.32 |

The testing procedures were as follows:

I. VARIOUS PRESERVATIVE TREATMENTS OF WOOD PRODUCT TO TEST PRESERVATIVE AND DEPTH OF PRESERVATIVE PENETRATION

Experiment A

Pole sections of white spruce, 7 in. diameter, 48 in. long were tested with the solution described in Example VI by pressure treatment. Specimens were loaded in a pressure vessel, which was evacuated to 26 in. Hg vacuum and maintained under vacuum for one hour. Then, the preservative solution was introduced into the pressure vessel and the pressure was increased up to 120 psi with compressed air and was maintained at that pressure for 5 hours. The temperature was increased up to 150° F. during treatment. After the pressure was released, the samples were kept for the next 12 hours immersed in the solution. The retention of the preservative solution in the treated specimens was determined. The depth of penetration in the middle of the samples was also measured on center cross-sections.

Experiment B

The treatment was carried out on white spruce pole sections 8 in. diameter and 48 in. long for each of the above preservative solution. The treating procedure was the same as described above, but the initial vacuum was held for 30 minutes only and for 5 hours at 115 psi pressure, during which time the specimens were immersed in the preservative solution. An additional period of 5 hours was used to keep the pole sections in the preservative solution without any pressure. The temperature during the pressure treatment was 155° F. The gross retention of the treating solution was determined and the depth of penetration, measured on center cross-sections, was measured.

Experiment C

Non-pressure treatment of white spruce lumber 2 × 4 × 48 inches by the preservative solutions described in Example VIII was achieved as follows: The treatment was carried out in the same manner as described above starting with an initial 1 hour vacuum, but in which no pressure was applied during 5 hours treatment when the lumber was immersed in the treating solution. The temperature was increased up to 175° F. in the treating cylinder and was held there for 5 hours. Cooling of the specimens in the preservative solution followed for the next 16 hours. The depth of penetration, on center cross-section, was measured.

Experiment D

The treating solution described in Example X was used to treat white spruce lumber and round wood specimens.

| Lumber | |
|---|---|
| Dimensions | 1.8 × 1.8 × 48 inches |
| Moisture content | 8 –10% |
| Round Wood (logs) | |
| Dimensions | 7 inches diameter × 48 inches long |
| Moisture content | 30% |

The specimens were loaded into a pressure vessel and evacuated to 26½ in. Hg and maintained under vacuum for 1 hour. The pressure was increased in the vessel to 10 in. Hg with ammonia gas before introducing sufficient treating solution completely to cover the specimens. The pressure in the treating vessel was raised to 100 psi with compressed air. The temperature of the treating solution was raised from 75° to 150° F. over the first 3-hour period and was reduced to 100° F. over the next 3 hours while maintaining an overpressure of 100 psi. The pressure was then reduced to 10 psi before pumping the treating solution back into a hold tank.

The retention of the treating solution in the wood specimens was determined 24 inches from the ends of the specimens.

Experiment E

The treating solution described above in Example VI was used to treat white spruce round wood specimens.

| Dimensions | 7 inches diameter × 48 inches long |
|---|---|
| Moisture content | 40% |

The specimens were loaded into a pressure vessel and evacuated to 26½ in. Hg and maintained under vacuum for 30 minutes. The vacuum was lowered to 20 in. Hg with ammonia gas for 10 minutes and then returned to 26½ in. Hg for a further 20 minutes. This process of flushing was repeated three times to give a total period of evacuation of 2 hours. The vacuum in the treating vessel was reduced to 1 in. Hg and the treating solution was added. The pressure in the vessel was raised to 100 psi with air and was maintained at this pressure for 5 hours to give a treating schedule of 7 hours.

Over the first 4 hours of the process (2 hours vacuum and 2 hours pressure), the temperature in the treating vessel was raised from 75° to 180° F. The temperature was reduced continuously over the last 3 hours of the process to 100° F.

The retention of treating solution and the depth of penetration in the wood specimens were determined 24 inches from the ends of the specimens.

In all the above Experiments (A-E) the liquid preservative retention was in the average in the range from 12 to 19 lb/ft³; preservative penetration on cross-sections ranged from 0.35 to 2.1 in. in the sapwood of ound wood and from 0.25 in. in lumber.

II. WATER REPELLENCY AND WATER UPTAKE BY TREATED WOOD

The water repellency of wood treated with each of the preservative solutions described was tested by measurement of the contact angle between the surface of treated wood and water. It was found that the compositions of embodiments of this invention provide treated wood which are more water repellent than other compositions including those conventionally used.

The water uptake by the white spruce treated with various preservative compositions of Examples I-XI revealed the water repellency of wood treated with various preservatives. The results show that wood treated with the compositions of aspects of this invention has a lower water uptake after treatment than wood treated with the traditional preservatives.

The penetration of various compositions of the present invention into non-treated white spruce (a difficult-to-penetrate refractory species), was carried out on oven dry samples of white spruce and, expressed by per cent liquid uptake, show that, as compared with traditional preservatives and when compared to distilled water, the compositions of aspects of this invention show faster and higher preservative penetration by wood samples, and approximately the same preservative penetration as for the best presently known preservatives.

III. RESISTANCE TO FUNGAL ATTACK

Compositions of aspects of his invention, represented by Examples VIII and X, were tested in comparison with Example VI (CAA), ammoniacal copper arsenite (ACA), chromated copper arsenate (CCA) and pentachlorophenol, according to AWPA Standard M10 LO (and ASTM standard D1413-61) in three experimental series, as follows: End-matched specimens were impregnated with preservative solutions of different concentrations. After drying, the blocks were sterilized and pairs of blocks treated with the preservatives were placed in jars containing 3-week old cultures of the test fungi. Two controls were used, one treated with distilled water, the other with distilled water containing ammonia. The jars were incubated for 12 weeks under standard conditions. Three pairs of blocks were used as a treatment group and the weight loss of wood was calculated from the oven dry weight of the wood after treatment, and before and after incubation. In the first series two test fungi were used: *Coniophora puteana* (A 328) and *Poria monticola* (A 189, Madison 698). This latter fungus is known for its tolerance to copper and zinc compounds and is recommended by both standards as a test fungus. For the second and third series, *Coniophora puteana* (A 328) and *Lenzites trabea* (Madison 53a) were used.

*Coniophora puteana* was selected on the basis of detoxication studies and toxicity tests carried out in this laboratory over the last several years. This fungus is a common cause of decay and is widespread throughout North America and Europe. It is used commonly throughout Europe and Australia as a test fungus as it grows well under a variety of conditions and shows a high level of resistance to a broad spectrum of fungicides. *Lenzites trabea* is a fungus tolerant to arsenic and is recommended for testing by the above standards.

The results of the tests are summarized in Table 1 below, where the threshold levels represent the lowest preservative salt retentions which permit up to the maximum 3% of weight due to decay.

Table 1

| | Average threshhold levels (oxides, lb/cu.ft.) | | | | | |
|---|---|---|---|---|---|---|
| | Test Series I | | Test Series II | | Test Series III | |
| Preservative | CON | POR | CON | LENZ | CON | LENZ |
| Ex. VI CAA | 0.08 | 0.05 | 0.12 | 0.05 | — | — |
| X CZAA(1:1) | — | — | — | — | 0.25 | 0.20 |
| VIII ZAA (AS¹) | 0.5 | 0.08 | — | — | 0.7 | 0.7 |
| CCA-C | — | — | — | — | 0.3 | 0.2 |
| ACA | — | — | 0.06 | 0.05 | 0.09 | 0.06 |
| pentachlorophenol | — | 0.3 | — | — | — | — |

CON - *Coniophora cerebella*
POR - *Poria monticola*
LENZ - *Lenzites trabea*

Summary of rounded-up threshhold levels (lbs/cu.ft.)

| | | |
|---|---|---|
| CAA | 0.1 | |
| CZAA (3:1) | 0.3 | preservative formulations according to aspects of this invention |
| ZAA | 0.7 | |
| CCA-C | 0.3 | |
| ACA | 0.1 | traditional preservatives |
| pentachlorophenol | 0.3 | |

IV. GLOW COMBUSTION RESISTANCE

Spruce samples were evenly penetrated by the preservative solution to provide the required retention of preservative salt after solvent evaporation. Preservative liquid uptake was calculated from weight before and after treatment of samples with preservative. Samples were dried and exposed to glowing in a china crucible placed over a burner flame, in exactly defined and reproducible conditions of exposure for 30 seconds.

After this exposure of the sample, the glowing combustion started and the sample was placed inside a closed container to eliminate additional air supply to the sample. When the chemical in the wood sample supported glowing combustion, the sample glowed and lost its weight up to 90-95%. When no chemical was present, the glowing of wood ceased and only about 25% weight loss was detected. The higher the weight loss the lower the glowing combustion resistance and vice versa.

In the testing of mixtures of the preservative system of aspects of this invention (CAA and ZAA) for glowing combustion resistance, the preservative salt retention wad adjusted to 0.4 lb/cu.ft., which is the minimum retention of preservative salt in oxide form for treated products in ground contact exposure (required by CSA 080 Standard for wood preservation). The volume ratio between CAA and ZAA varied from 3:1 to 1:3. Samples with no preservative salt were included as a control. Chromated copper arsenate (CCA-C) and ammoniacal copper arsenate (ACA) were also tested as a representative of traditional water-borne preservatives. Six samples for each preservative were tested and duplicated in two experimental series. The results of average weight loss are summarized in the table.

| Weight losses of treated spruce samples exposed to glowing combustion | | |
|---|---|---|
| Preservative | Average Weight Loss (%) | Glowing combustion resistance |

1) Traditional systems

-continued

| Weight losses of treated spruce samples exposed to glowing combustion | | | |
|---|---|---|---|
| Preservative | | Average Weight Loss (%) | Glowing combustion resistance |
| CCA-C | | 87 – 96 | minimum |
| ACA | | 75 – 92 | minimum |
| CAA | | 76 – 92 | minimum |
| 2) New System | | | |
| CAA + ZAA | 75:25 | 77 | minimum |
| | 50:50 | 60 | medium |
| | 45:55 | 56 | medium |
| | 40:60 | 56 | medium |
| | 35:65 | 29 | maximum |
| | 25:75 | 27 | maximum |
| ZAA | | 22 | maximum |
| 3) Control | | 21 – 29 | maximum |

It is seen that the glowing combustion resistance after treatment with the traditional preservative was minimal, while the glowing combustion resistance after treatment with compositions comprising mixtures of CAA and ZAA according to aspects of the present invention was either medium or maximum (except for the ratio of CAA:ZAA of 3:1).

V. ARSENIC LEACHABILITY

All eleven preservatives described in Examples I-XI were evaluated using 10 blocks ⅜ (tangentially) × ½ inch in cross-section and 1 inch long.

The blocks were then oven dried, immersed in the appropriate preservative solution, and subjected intermittently to a vacuum of 26 in. of mercury for 8 hours. They were then air dried for 18 hours, and oven dried for 6 hours (to constant weight) to ensure good fixation of preservative in the wood substance. The oven dry weight of each block was recorded before and after treatment. The whole of each block was then microtomed into sections 40 to 60 m$\mu$ thick which were stored in sealed glass containers until they were leached. The concentration of treating solution was not checked after treatment. However, each set of 10 blocks was treated in freshly prepared preservative and 500 ml of preservative solution was used for each treatment.

The leaching procedure used was fast and yet provided severe leaching conditions. An enlarged area of treated wood by cutting it into microsections was used. In order to identify differences within a family of preservatives all having good leach resistance, even though they may not approximate short service life conditions. The test apparatus used was simple and could be reproduced to enable a large number of leaching tests to be carried out simultaneously. A modified "Soxhlet" extractor was chosen for this reason. This consisted of an extractor to which additional cooling coils were added around the condenser. This was done to reduce the temperature of the extracting water to 80°±6° C. Each sectioned sample block was leached for 24 hours in a glass thimble by 250 ml of distilled water recirculated through the Soxhlet extractor at a flow rate of 58 to 63 ml/hour.

Atomic absorption spectrophotmetry was chosen as the analytical tool because it provides rapid and precise analysis of aqueous solutions with low concentrations of ions. The loss of copper, chromium, zinc, and arsenic from the treated wood blocks was determined by measuring the amounts of these elements which appeared in the leaching water.

Copper and zinc contents in leaching water were determined on a Perkin-Elmer AAS Model 303 using an air-acetylene flame at 324.7 and 213.9 nm, respectively.

The arsenic content was determined by the same instrument using an argon-hydrogen flame at 193.7 nm. Each sample of leaching water was analyzed twice and the average value used.

Concentration of arsenic in nine treating solutions was adjusted to the same level so that the same conditions of preservative treatment resulted in very similar levels of arsenic retention in the samples before leaching. From the retention of preservative solution (listed below) and its composition as described hereinabove, an exact content of elements (Cu, Zn and As) in wood samples was calculated.

Average oxide retention (in lb/ft$^3$) in preservative solutions:

| | |
|---|---|
| ZMA-(As$^{III}$) | 0.85 |
| ACA-(As$^{III}$) | 1.00 |
| CuAs-(As$^V$) | 0.86 |
| St$_{CCA-C}$-(As$^V$) | 1.09 |
| St$_{CAA}$-(As$^V$) | 1.47 |
| CAA-(As$^V$) | 2.03 |
| ZAA-(As$^{III}$) | 2.46 |
| ZAA-(As$^V$) | 2.48 |
| CZAA(3:1)-(As$^V$) | 2.12 |
| CZAA(1:1)-(As$^V$) | 2.56 |
| CZAA(1:3)-(As$^V$) | 2.41 |

The leached out elements were determined by atomic absorption spectrophotometry from a leaching water which was, in all series, a clear water solution, without any precipitate or discoloration. No deposit of extracted elements was detected on the walls of flasks collecting the leaching water, as determined by an additional atomic absorption spectrophotometry.

The results are summarized in the tables below.

TABLE 2

| Leaching of Elements from Treated Spruce | | | | | |
|---|---|---|---|---|---|
| | Ex. I | Ex. II | Ex. III | Ex. IV | Ex. V |
| | ZMA | ACA | CuAs | St$_{CCA-C}$ | St$_{CAA}$ |
| Cu mg | | 28.58 | 11.93 | 22.01 | 28.60 |
| % | — | 1.9 | 2.4 | 1.1 | 2.1 |
| As mg | 22.45 | 23.43 | 17.92 | 17.37 | 23.3 |
| % | 67.3 | 48.0 | 53.3 | 34.7 | 38.9 |
| Zn mg | 9.76 | — | — | — | — |
| % | 2.7 | — | — | — | — |
| | Ex. VI | Ex. VII | Ex. VIII | Ex. IX | Ex. X | Ex. XI |
| | CAA | ZAA (As$^{III}$) | ZAA (As$^V$) | CZAA (3:1) | CZAA (1:1) | CZAA (1:3) |
| Cu mg | 49.60 | | | 36.80 | 24.99 | 12.30 |
| % | 3.1 | — | — | 2.3 | 4.0 | 4.1 |
| As mg | 23.70 | 23.30 | 22.80 | 23.40 | 23.83 | 23.70 |
| % | 15.4 | 9.7 | 3.5 | 7.2 | 2.6 | 1.3 |
| Zn mg | | 72.31 | 70.50 | 18.10 | 36.93 | 53.8 |
| % | — | 0.8 | 0.7 | 0.9 | 1.1 | 1.2 | mg - average amount of element available in samples for leaching
% - average percent of element leached

TABLE 3

| Percent Arsenic Leached from Treated Spruce with Statistical Differences ("t" values in brackets) | | | | | | |
|---|---|---|---|---|---|---|
| Ex. I | | Ex. III | | Ex. II | | |
| ZMA | ** | CuAs | NSD | ACA | *** | |
| 67.3 | (3.61) | 53.3 | (1.52) | 48.0 | (12.85) | |
| | | | | * | | |
| | | | | (2.38) | | |
| | | | | Ex. V | | |
| | | CuAs | ** | St$_{CAA}$ | *** | |
| | | 53.3 | (3.75) | 38.9 | (7.82) | |
| Ex. VI | | Ex. VII | | Ex. VIII | | |
| CAA | *** | ZAA (As$^{III}$) | *** | ZAA (As$^V$) | *** | CZAA (1:3) |
| 15.4 | (4.03) | 9.7 | (4.84) | 3.5 | (6.20) | 1.3 |
| | | NSD | | * | | |
| | | (1.89) | | (2.41) | | |
| | | Ex. IX | | Ex. X | | Ex. XI |

TABLE 3-continued

| CAA | *** | CZAA (3:1) | *** | CZAA (1:1) | ** | CZAA (1:3) |
|---|---|---|---|---|---|---|
| 15.4 | (10.71) | 7.2 | (9.12) | 2.6 | (3.26) | 1.3 |

\* - significant difference at the 95% probability
\*\* - significant difference at the 99% probability
\*\*\* - significant difference at the 99.9% probability
NSD - no significant difference Data on the leaching of elements from spruce treated with the various copper-zinc-arsenic preservatives are summarized in Tables 2 and 3.

The fixation of copper or zinc is good so the leaching reaches only low values (1 to 4% approximately) for all preservatives tested. On the other hand, a significant improvement was found in the leaching of arsenic when the wood was treated with preservative formulations according to aspects of this invention. It is noted from Tables 2 and 3 that while the leaching of some prior art formulations is between 67.3% and 38.9%, only 15.4 to 1.3% of arsenic is leached from the formulations of aspects of this invention.

An important aspect of the present invention is that the preservative compositions should have a weight ratio of metal oxide/arsenic oxide of 1.5 or more, e.g. 1.71–2.92. The trend between leaching of arsenic and the ratio of oxide is illustrated in the single figure where this correlation is significant at the 99.9% probability level (correlation coef. $r = -0.915$). The pentavalent arsenic in the formulations provided better fixation than the trivalent, at the same element retentions in the tested samples. This can also be seen from the single FIGURE where the preservative formulations with trivalent arsenic show higher leaching (see circled points).

Ammonium bicarbonate and/or other carbonates are necessary to keep the excess of metal oxide in the solution. The low ratios of ammonium bicarbonate and/or carbonates/metal oxide, such as used in the preservative formulations of aspects of this invention do not adversely influence the arsenic fixation. It was shown in additional experiments that an excess of ammonium bicarbonate and/or other carbonates over the metal oxide, such as 4 times and higher, considerably increases arsenic leaching, and therefore should be avoided.

It is therefore seen that the fixation of Cu or Zu is exceptionally good, so the leaching is very low, approximately 1–4%. The leaching of arsenic from wood is considerably influenced by the composition of the preservative solution. In order to provide the improved leaching retention levels, it is essential to have a metal oxide/arsenic oxide ratio of 1.5 or more. The trivalent arsenic leaches more than the pentavalent, from samples treated to the same arsenic retention, in both types of preservatives containing either zinc-copper-arsenic or zinc-arsenic in the formulation. The preservative formulations of aspects of this invention (ZAA and CZAA) characterized by the metal oxide/arsenic oxide weight ratio of 1.5 or more than a very low average leaching of arsenic (from 1.3 to 15.4% for various formulations). The ZAA system has leach resistance of As up to 4.4 times better than the CAA. Further improvements of the leaching resistance of arsenic from CAA treated wood are achieved by especially preferred compositions involving gradually increasing the admixture of ZAA formulations to the CAA in volume ratios, CAA/ZAA of 3:1, 1:1 and 1:3 and thus lowering the average leached amount to 7.2, 2.6 and 1.3% accordingly.

Examples XII–XIV

Three additional preservative solutions were tested in two parallel experiments for the element leaching from spruce as described hereinabove.

Two new ammoniacal metal complex perservatives according to aspects of this invention were compared with one CCA formulation. The pH of the model CCA formulation was lower than that used in commercial practice but its composition corresponded to the AWPA Standard for CCA-C (47.5% $CrO_3$, 18.5% CuO, 34% $As_2O_5$). The two solutions of aspects of this invention were aqueous, ammoniacal complexes of metal arsenate, metal carbonate salt systems in which the proportion of arsenate ion to carbonate ion had been selected on the basis of screening tests with respect to toxicity, water repellency, and leach resistance. These formulations are referred to here as the copper-ammonia-additive (CAA) system and the zinc-ammonia-additive (ZAA) system. Their compositions correspond with the oxide content of metal and arsenic to those as described in Examples VI and VIII, respectively. Their compositions, along with that of the CCA preservative, used as standard for comparison, are shown below. This model CCA formulation (oxide form) has been found to be relatively well fixed from the family of the commercial CCA preservatives.

CCA-C (oxide based)
  16.04 g $CrO_3$
  6.24 g CuO
  11.48 g $As_2O_5$ filled up to 1000 ml with $H_2O$;
  3.4 percent salts on oxide basis;
  pH = 1.34

CAA
  35 g $CuCO_3.Cu(OH)_2$
  18 g $NH_4HCO_3$
  250 ml $NH_4OH$ (26% $NH_3$)
  20 g $H_3A_5O_4$ (71% $As_2O_5$)
  filled up to 1000 ml with $H_2O$;
  3.9 percent salts on oxide basis ZAA
  35.7 g ZnO
  41.2 g $NH_4HCO_3$
  200 ml $H_3A_5O_4$ (71% $As_2O_3$)
  diluted 1 + 4 by $H_2O$;
  5.0 percent salts on oxide basis The preservative salt retention of the three above-described solutions is tabulated below in Table 4:

Table 4

| Preservative | Experiment | Percent of Salt in Wood (w/w Oven Dry) | | | Average Salt Retention on oxide basis (pcf) |
|---|---|---|---|---|---|
| | | Minimum | Average | Maximum | |
| CCA (oxide-based) | I | 6.09 | 6.84 | 8.13 | 1.39 |
| | II | 4.88 | 6.23 | 6.83 | 1.42 |
| CAA | I | 9.65 | 10.53 | 11.37 | 1.76 |
| | II | 11.16 | 12.15 | 13.06 | 2.10 |
| ZAA | I | 12.16 | 12.94 | 13.87 | 2.22 |
| | II | 11.41 | 13.82 | 16.86 | 2.22 |

The preservative elements leached from spruce samples in a 24-hour Soxhlet extraction are tabulated below in Table 5.

Table 5

| Preservative | Experiment | | Leached Element | | | |
|---|---|---|---|---|---|---|
| | | | Cr | Cu | As | Zn |
| CCA | I | mg available | 16.97 | 10.16 | 15.25 | |
| | | mg leached | 0.24 | 2.58 | 2.65 | |
| | | percent leached | 1.4 | 25.4 | 17.4 | |
| | II | mg available | 13.98 | 8.38 | 12.57 | |
| | | mg leached | 0.03 | 2.41 | 2.33 | |
| | | percent leached | 0.2 | 28.7 | 18.5 | |
| CAA | I | mg available | | 43.58 | 20.15 | |
| | | mg leached | | 0.48 | 1.97 | |
| | | percent leached | | 1.1 | 9.8 | |
| | II | mg available | | 41.40 | 18.70 | |
| | | mg leached | | 1.16 | 2.36 | |
| | | percent leached | | 2.8 | 12.6 | |
| ZAA | I | mg available | | | 16.67 | 51.61 |
| | | mg leached | | | 0.27 | 0.46 |
| | | percent leached | | | 1.6 | 0.9 |
| | II | mg available | | | 16.13 | 50.20 |
| | | mg leached | | | 0.50 | 0.35 |
| | | percent leached | | | 3.1 | 0.7 |

These results show that more arsenic was leached from spruce treated with CCA formulation than from wood treated with the new CAA and ZAA formulations. The amount of copper leached from the CCA-treated wood was also higher than that from CAA-treated wood. CAA arsenic leached was approximately two-thirds and ZAA arsenic approximately one-fifth as much as the arsenic leached from wood treated with the CCA. The ZAA formulation showed exceptional leaching resistance for both zinc and arsenic.

The preservative solutions (CAA) and (ZAA and CZAA) of aspects of this invention tested above show high leach resistance. The metal Zn or Zn + Cu is extremely well fixed in the systems ZAA and CZAA. The best fixation of arsenic in the series tested was in the ZAA system.

A summary of the test results for the 14 compositions tested is given below in Table 6.

Table 6

| | Prior Art | | | Compositions of Aspects of this Invention | |
|---|---|---|---|---|---|
| | CCA-C | ACA | CAA | CZAA (1:1) | ZAA |
| Properties of treated wood | | | | | |
| toxicity to food decaying fungi | ++ | ++ | ++ | ++ | + |
| water repellency | ++ | − | ++ | ++ | + |
| leaching resistance | + | (±) | + | ++ | ++ |
| glowing combustion resistance | − | − | − | + | ++ |
| natural appearance color | + | (±) | (±) | (±) | ++ |
| paintability | ++ | + | + | + | + |
| Properties of treating solution | | | | | |
| ability to penetrate refractory species | − | ++ | ++ | ++ | ++ |
| stability in processing | (±) | + | + | + | + |

Index:
++ = very good or reliable property, or meeting required standards
+ = moderately good property
(±) = not distinctly good property, or variable property
− = poor property or not meeting recognized standards
CCA = chromated copper arsenate
ACA = ammoniacal copper arsenate
CAA = copper-arsenic-additive system
CZAA = copper-zinc-arsenic-additive system
ZAA = zinc-arsenic-additive system Comparative Tests Formulations comprising CAA containing Cu and As having various ratios of metal oxide to arsenic oxide and $CO_2$ to metal were tested for resistance to leaching in comparison with the formulations of aspects of this invention, namely ZAA and CZAA containing various ratios of metal oxides to arsenic oxide and $CO_2$ to metals. The arsenic content in all the formulations (i.e. 1.42 g/100 ml volume) was the same as in formulations defined herein in Examples VI and VII–XI. Also the arsenic retention in spruce samples before the leaching was in the same range as in the above-mentioned formulations of Examples VI and VIII—XI. The results are shown below in Table 7.

Table 7

| | CAA | | CZAA | | | ZAA |
|---|---|---|---|---|---|---|
| | 1 | 2 | (3:1) | (1:1) | (1:3) | (As') |
| Me oxide As oxide | 1.71 | 2.18 | 1.91 | 2.11 | 2.32 | 2.51 |
| $CO_2$ Me | 0.88 | 1.34 | 0.84 | 0.82 | 0.81 | 0.80 |
| As leaching | | | | | | |
| % Oven Dried | 15.4 | 7.6 | 7.2 | 2.6 | 1.3 | 3.5 |
| % Air Dried | 17.9 | 7.6 | 5.8 | 3.3 | 1.8 | 3.3 |

Illustrative compositions of aspects of this invention were formulated in a series where the metal oxide/arsenic oxide increased from 1.91 up to 2.51. It was found that the arsenic leaching decreased when the ratio metal oxide/arsenic oxide increased (leaching decreased from about 7 to about 1%). Comparative formulations with about the same metal oxide/arsenic oxide ratio with and without zinc (for example CAA-2, against CZAA(1:1) in Table 7). The formulation containing the zinc along with the copper (CZAA, 1:1) leached less arsenic (only about 3%) while the formulation containing only copper (CAA-2) leached more arsenic (about 8%). The combination of copper and zinc was also better than the zinc alone, indicating some synergism with both metals present. These comparative tests illustrate that the formulations outside the scope of this invention do not provide good fixation and low leaching of arsenic when tested in comparable conditions with formulations of aspects of this invention.

In the preceding Examples for the CAA/ZAA volume ratios 3:1, 1:1 and 1:3, the weight percent of Cu based on total Cu + Zn is 60, 40 and 19, respectively. It is within the scope of broad aspects of this invention to have Cu present in amounts up to about 75% (by weight of total metal) and still derive significant benefits in terms of arsenic leaching resistance due to the presence of zinc. The 75% level for Cu roughly corresponds to a CAA/ZAA ratio of 4:1.

Instead of applying the treating solution uniformly to the surface (with or without pressure) one or more holes can be drilled into the wood while in service and the solution introduced as a concentrate (as described on pages 7 and 8 hereinabove) into the hole. Normally the hole will slant in a downward direction, allowing the entire hole to be filled with solution one or more times. Test results have shown wide diffusion of active components in the surrounding wood.

The preceding examples can be repeated with similar success by substituting the generically and specifically described reactants and operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A wood treating composition comprising an aqueous solution containing:
    a. soluble component adapted to form a normally water-insoluble compound of zinc or zinc and copper with arsenic acid or arsenious acid, the metal being present in an amount of 0.1–4% by weight (as Zn or Zn + Cu metal) of the total aqueous solution, the weight ratio of zinc or zinc and copper (as oxides) to arsenic (as oxides) being 1.5 or more;
    b. 0.15–10% by weight of the total aqueous solution of a water repellent component comprising at least one of carbonate and bicarbonate ions, in an amount of up to 150% of the zinc or zinc and copper, the weight ratio of $CO_2/NH_3/Zn/As$ or of $CO_2/NH_3/Zn + Cu/As$ being 1.7–2.3/5.9–6.7/1.-9–2.9/0.9; and
    c. ammonia, in an amount of 1–28% by weight of the total aqueous solution; the ammonia being sufficient to solubilize the normally water-insoluble salts of zinc or zinc and copper and the normally water-insoluble water repellent component.

2. The wood treating composition of claim 1 comprising:
    a. zinc ammonium cations;
    b. arsenic or arsenious anions; and
    c. anions of a carbonate or a bicarbonate.

3. The wood treating composition of claim 1 having a pH of 9 or more, and comprising an aqueous solution containing:
    a zinc ammonium cations and copper ammonium cations;
    b. arsenic or arsenious anions; and
    c. anions of a carbonate or a bicarbonate.

4. The wood treating composition of claim 1 containing carbonates of zinc or zinc and copper.

5. The wood treating composition of claim 1 wherein the composition contains zinc arsenate or zinc arsenite.

6. The wood treating composition of claim 1 wherein the composition contains zinc arsenate and copper arsenate or zinc arsenite and copper arsenite.

7. The wood treating composition of claim 3 comprising: (A) from 1 to 4 parts by volume of a composition comprising (a) copper ammonium cations, (b) arsenic or arsenious anions, and (c) anions of a carbonate or a bicarbonate; and (B) 1 part by volume of a composition comprising (a) zinc ammonium cations, (b) arsenic or arsenious anions and (c) anions of a carbonate or a bicarbonate, the Cu being present in up to about 75% by weight based on total metal.

8. The wood treating composition of claim 3, comprising: (A) 3 parts by volume of a composition comprising (a) copper ammonium cations, (b) arsenic or arsenious anions, and (c) anions of a carbonate or a bicarbonate; and (B) 1 part by volume of a composition comprising (a) zinc ammonium cations, (b) arsenic or arsenious anions and (c) anions of a carbonate or a bicarbonate, the Cu being present in about 60% by weight based on total metal.

9. The wood treating composition of claim 3 comprising: (A) 1 part by volume of a composition comprising (a) copper ammonium cations, (b) arsenic or arsenious anions, and (c) anions of a carbonate or a bicarbonate; and (B) 1 part by volume of a composition comprising (a) zinc ammonium cations (b) arsenic or arsenious anions, and (c) anions of a carbonate or a bicarbonate, the Cu being present in about 40% by weight of total metal.

10. The wood treating composition of claim 3 comprising: (A) 1 part by volume of a composition comprising (a) copper ammonium cations, (b) arsenious anions, and (c) anions of a carbonate or a bicarbonate; and (B) 3 parts by volume of a composition comprising (a) zinc ammonium cations, (b) arsenic or arsenious anions, and (c) anions of a carbonate or a bicarbonate, the Cu being present in about 19% by weight of total metal.

11. The wood treating composition of claim 1 selected from the group consisting of:

| | | |
|---|---|---|
| (a) | arsenic oxide ($As^V$) | 1.4 parts by weight |
| | zinc oxide | 3.6 parts by weight |
| | $NH_4HCO_3$ | 4.0 parts by weight |
| | aqueous ammonia solution (28% $NH_3$, 20 ml in 100 ml $H_2O$) | 91.0 parts by weight |
| (b) | arsenic oxide ($As^V$) | 1.4 parts by weight |
| | copper oxide | 1.8 parts by weight |
| | zinc oxide | 1.0 parts by weight |
| | ammonium bicarbonate | 2.4 parts by weight |
| | aqueous ammonia solution (28% $NH_3$, 23.7 ml in 100 ml $H_2O$) | 93.4 parts by weight |
| (c) | arsenic oxide ($As^V$) | 1.4 parts by weight |
| | copper oxide | 1.2 parts by weight |
| | zinc oxide | 1.8 parts by weight |
| | aqueous ammonia solution (28% $NH_3$, 22.5 ml in 100 ml $H_2O$) | 95.6 parts by weight |
| and (d) | arsenic oxide ($As^V$) | 1.4 parts by weight |
| | copper oxide | 0.6 parts by weight |
| | zinc oxide | 2.7 parts by weight |
| | $NH_4HCO_3$ | 3.5 parts by weight |
| | aqueous ammonia solution (28% $NH_3$, 21.2 ml in 100 ml $H_2O$) | 91.8 parts by weight |

12. A concentrated, aqueous wood treating composition comprising a solution, in concentrated ammonia, of:
    a. ammoniacal-solution soluble components adapted to form a normally water-insoluble compound of zinc or of zinc and copper with arsenic acid or arsenious acid, the metal being present in an amount of 4–15% by weight (as Zn or Zn + Cu metal) based on the volume of the aqueous solution, the weight ratio of zinc or zinc and copper (as oxides) to arsenic (as oxides) being 1.5 or more;
    b. a water repellent component comprising at least one of carbonate and bicarbonate ions, in an amount of up to 150% by weight of the zinc or zinc and copper, the weight ratio of $CO_2/NH_3/Zn/As$ or of $CO_2/NH_3/Zn + Cu/As$ being 1.7–2.3/5.9–6.7/1.-9–2.9/0.9, the total solids being from about 15 to about 45% by weight, based on the volume of the aqueous solution; and
    c. the ammonia being sufficient to solubilize the normally water-insoluble salts of zinc or of zinc and copper and the normally water-insoluble water repellent component.

13. A procedure for protecting wood in service which comprises: providing at least one hole in said wood; and introducing a concentrated solution as claimed in claim 12 into said hole, thereby to obtain wide diffusion of active components then dryng such wood with the resulting loss of ammonia and high fixation of arsenic.

* * * * *

UNITED STATES PATENT AND TRADEMARK OFFICE
CERTIFICATE OF CORRECTION

PATENT NO. : 4,038,086
DATED : July 26, 1977
INVENTOR(S) : MICHAEL R. CLARKE et al It is certified that error appears in the above-identified patent and that said Letters Patent are hereby corrected as shown below:

Column 1, line 9: replace "3,945,935" with --- 3,945,835 ---.

Column 7, line 53: replace "formation" with --- formulation ---.

Columns 7-9, Examples I - XI: in each, replace "ratio $\frac{\text{metal oxide}}{\text{arsenic oxide}}$ in formulation" with --- ratio $\frac{\text{metal oxide}}{\text{arsenic oxide}}$ in formulation ---.

Column 9, lines 2-3: delete all three headings; over the two final columns, insert as headings: --- $\frac{\text{ZAA}}{(\text{AsIII})}$ --- and --- $\frac{\text{ZAA}}{(\text{AsV})}$ ---, respectively.

Column 10, line 15: replace "speimens" with --- specimens ---.

Column 11, line 40: delete "LO".

Column 15, line 46: replace "Zu" with --- Zn ---.

UNITED STATES PATENT AND TRADEMARK OFFICE
CERTIFICATE OF CORRECTION

PATENT NO. : 4,038,086
DATED : July 26, 1977
INVENTOR(S) : MICHAEL R. CLARKE et al It is certified that error appears in the above-identified patent and that said Letters Patent are hereby corrected as shown below:

Column 8, line 15: delete "(g/".

Column 10, lines 29-30: replace "completely to cover the specimens" with --- to cover the specimens completely ---.

Column 11, line 4: replace "ound" with --- round ---.

Column 16, lines 22 and 23: replace "ammonia" (two occurrences) with --- arsenic ---.

Column 16, lines 43 and 50: replace "$H_3A_5O_4$" with --- $H_3AsO_4$ ---.

Column 17, line 48: in Table 6, line 1, replace "food" with --- wood ---.

UNITED STATES PATENT AND TRADEMARK OFFICE
CERTIFICATE OF CORRECTION

PATENT NO. : 4,038,086
DATED : July 26, 1977
INVENTOR(S) : MICHAEL R. CLARKE et al It is certified that error appears in the above-identified patent and that said Letters Patent are hereby corrected as shown below:

Column 18, lines 20 and 21, Table 7: "$\text{Me oxide} \atop \text{As oxide}$" and "$CO_2 \atop Me$" should be rewritten as --- $\dfrac{\text{Me oxide}}{\text{As oxide}}$ --- and --- $\dfrac{CO_2}{Me}$ ---, respectively.

Column 19, line 13: in Claim 1, "component" should be replace with --- components ---.

Signed and Sealed this

Twentieth Day of June 1978

[SEAL]

Attest:

RUTH C. MASON
*Attesting Officer*

DONALD W. BANNER
*Commissioner of Patents and Trademarks*